US008652805B2

(12) United States Patent
Balagurusamy et al.

(10) Patent No.: US 8,652,805 B2
(45) Date of Patent: Feb. 18, 2014

(54) TRAPPING MOLECULAR SEGMENTS IN NANO-GAPS

(75) Inventors: Venkat S. K. Balagurusamy, Suffern, NY (US); Stanislav Polonsky, Putnam Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 164 days.

(21) Appl. No.: 13/209,582

(22) Filed: Aug. 15, 2011

(65) Prior Publication Data
US 2013/0043131 A1 Feb. 21, 2013

(51) Int. Cl.
*G01N 27/447* (2006.01)

(52) U.S. Cl.
USPC ........................ 435/68.1; 435/287.3; 204/451

(58) Field of Classification Search
USPC ........................ 204/450–453, 518, 600–604; 435/287.2, 288.2, 288.6, 50, 68.1, 99; 977/963
See application file for complete search history.

(56) References Cited

U.S. PATENT DOCUMENTS

| | | | |
|---|---|---|---|
| 5,665,216 | A | 9/1997 | Karger et al. |
| 7,355,216 | B2 | 4/2008 | Yang et al. |
| 7,390,463 | B2 | 6/2008 | He et al. |
| 7,625,706 | B2 | 12/2009 | Akeson et al. |
| 7,678,562 | B2 | 3/2010 | Ling |
| 2010/0035260 | A1 | 2/2010 | Olasagasti et al. |
| 2011/0223652 | A1* | 9/2011 | Peng et al. .................. 435/287.2 |

OTHER PUBLICATIONS

S. D. Gillmor et al., "Hydrophilic/Hydrophobic Patterned Surfaces as Templates for DNA Arrays," Langmuir, vol. 16, 2000, pp. 7223-7228.
J. J. Kasianowicz et al., "Characterization of Individual Polynucleotide Molecules Using a Membrane Channel," Proc. Natl. Acad. Sci. USA, vol. 93, 1996, pp. 13770-13773.
I.-F. W. Kuo et al., "An ab Initio molecular dynamics study of the aqueous liquid-vapor interface," Science, vol. 303, 2004, pp. 658-660.
B. Neumcke et al., "Nonlinear Electrical Effects in Lipid Bilayer Membrane," Biophysical Journal, vol. 9, Issue 9, 1969, pp. 1160-1170.
S. Polonsky et al., "Nanopore in metal-dielectric sandwich for DNA position control," Appl. Phys. Lett., vol. 91, 2007, 153103.
S.K. Cho, H. Moon, and C-.J. Kim, "Creating, Transporting, Cutting, and Merging Liquid Droplets by Electrowetting-Based Actuation for Digital Microfluidic Circuits", 2003 Journal of Microelectromechanical Systems, 12, 70-80.
Israelachvili, J.N., Intermolecular and surface forces (Academic Press, 1985), pp. 28-29.
Mugele, F. and Baret, J.C., "Electrowetting: from basics to applications", J. Phys.: Condens. Matter 2005, 17, R705-R774.

* cited by examiner

*Primary Examiner* — J. Christopher Ball
(74) *Attorney, Agent, or Firm* — Cantor Colburn LLP; Vazken Alexanian

(57) ABSTRACT

A molecule trapping method includes forming a fluid bridge between a first reservoir and a second reservoir, translocating a molecule from the first reservoir to the second reservoir through the fluid bridge, detecting when a segment of the molecule is in the fluid bridge, breaking the fluid bridge and forming an a gap between the first and the second reservoirs, thereby trapping a segment of the molecule in the gap and making measurements on the segment of the molecule.

7 Claims, 10 Drawing Sheets

TRAPPING MOLECULAR SEGMENTS IN NANO-GAPS

BACKGROUND

The present invention relates to controlling the position of a single molecule, and more specifically, to systems and methods for trapping a segment of a linear polymer molecule in a nano-gap in the vicinity of a measurement instrument.

Molecules such as proteins, deoxyribonucleic acid (DNA) and ribonucleic acid (RNA) are long linear polymers including several charged molecular segments (e.g., nucleotides). In order to analyze these types of linear molecules, it is desirable to isolate and take measurements of the individual components of the molecule. The segment of interest should be locked in place for some time, which is sufficient for the instrument to characterize this segment of the linear polymer molecule.

SUMMARY

Exemplary embodiments include a molecule trapping method, including forming a fluid bridge between a first reservoir and a second reservoir, translocating a molecule from the first reservoir to the second reservoir through the fluid bridge, detecting when a segment of the molecule is in the fluid bridge, breaking the fluid bridge and forming an a gap between the first and the second reservoirs, thereby trapping a segment of the molecule in the gap and making measurements on the segment of the molecule.

Additional exemplary embodiments include a molecule trapping system, including a first reservoir, a second reservoir coupled to the first reservoir, wherein a gap disposed between the first and second reservoirs is configured to support a fluid bridge; and a first voltage source in electrical communication with the first reservoir and the second reservoir.

Further exemplary embodiments include a molecule trapping system, including a first reservoir, a second reservoir coupled to the first reservoir, wherein a gap disposed between the first and second reservoirs is configured to support a fluid bridge, a voltage source in electrical communication with the first reservoir and the second reservoir and a controller configured to apply direct the voltage source to apply a voltage to the first reservoir and the second reservoir.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In exemplary embodiments, the systems and methods described herein trap a segment of a charged linear polymer molecule in a nano-gap (hereinafter "gap") in the vicinity of a measurement instrument. The segment of interest is locked in place for a sufficient time for the instrument to characterize the segment of the linear polymer molecule. The systems and methods described herein implement controlled translocation of the linear molecule through the measuring instrument. The polymer can be locked and translocated with single monomer accuracy. The exemplary systems and methods described herein can be applicable to all linear polymers carrying localized charges along their backbone. For example, it is applicable to DNA or RNA molecules, which are charged polymers in solution, carrying negative electrical charge on the phosphate groups along their backbone. The systems and methods described herein implement a nano-scale gap between two reservoirs to lock the positions of the charges.

Figure 1:
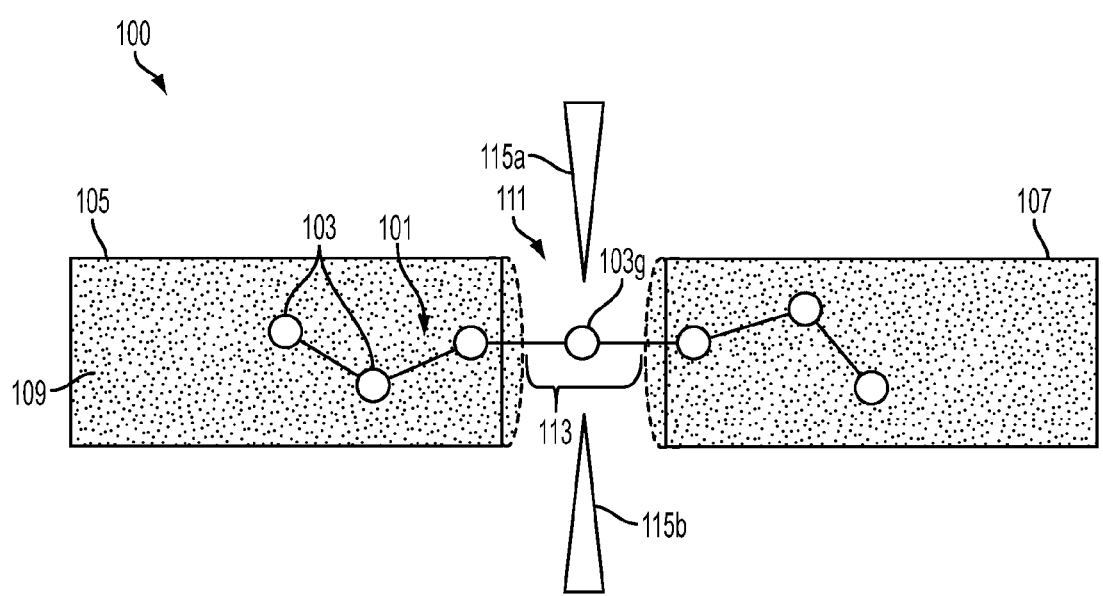
FIG. 1 diagrammatically illustrates an exemplary system 100 for trapping a segment of a molecule.

FIG. 1 diagrammatically illustrates an exemplary system 100 for trapping a segment of a molecule. The system 100 can include a first reservoir 105 and a second reservoir 107, each of the reservoirs 105, 107 including a solution 109. The reservoirs 105, 107 are separated by a gap 111, filled with gas or another solution. The system 100 can further include a measurement instrument 115a, 115b positioned adjacent to the gap 111. In exemplary embodiments, a molecule 101 can be disposed and translocated within the reservoirs 105, 107 and gap 111 as further described herein. For illustrative purposes the molecule 101 is described as a charged linear polymer schematically shown as a string with charges shown as circles 103. However, it will be appreciated that the molecule can be any molecule with charged groups. The molecule 101 can be stretched between the reservoir 105 and the second reservoir 107. The solution 109 within the reservoirs 105, 107 can have a sufficiently high relative dielectric permittivity $\in 1$. For example, the solution 109 can be water with $\in 1=80$. The solution or gas disposed within the gap 111 can have a dielectric permittivity $\in 2$, in which $\in 1 >> \in 2$. If the gap 111 is filled with another solution, it is desirable that the solution in the gap 111 be immiscible with the solution 109 inside the reservoirs 105 and 107. In this configuration, a segment 113 of the polymer 101 bridges the gap 111, exposing a number of its charges $103g$ to the gap medium. Any number of charges (i.e., zero, one two or more) can reside inside the gap 111. It is well known that the energy of a charge solvated in a liquid (fluid) with dielectric permittivity $\in$ scales as $\propto 1/\in$. Since $\in 1 >> \in 2$, the system 100 minimizes its energy by minimizing the number of charges 103g inside the gap. As such, the gap 111 "stretches" the segment 113. The stretching is illustrated in FIG. 1 by showing the segment 113 as a straight line while the rest of the molecule 101 disposed in the reservoirs 105, 107 is illustrated as a zigzagged line. In exemplary embodiments, under certain conditions, described further herein, the gap 111 can trap the charges 103g of the molecule 101, preventing the segment 113 from moving through the gap 111. Trapping and stretching of the segment 113 allows positioning of the segment 113 proximate to the measurement instrument 115a, 115b for a time interval sufficient to perform reliable measurements of the segment. For example, if the molecule 101 is a single stranded DNA molecule, the measurement 115a, 115b instrument can identify the type of the monomer (Adenine, Thymine, Cytosine, or Guanine). The structure of the measurement instrument 115a, 115b implies measurement of the transverse tunneling current through molecule 101. In practice, one can use any other technique, either electrical or optical.

Figure 2A:
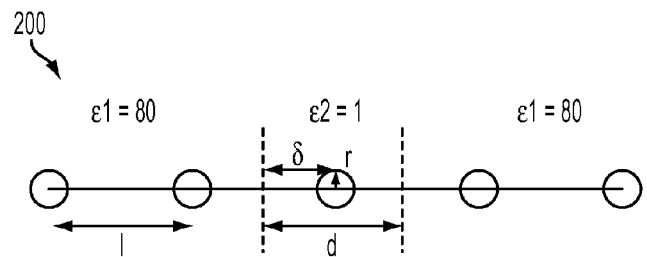
FIG. 2A illustrates the parameters used in calculating trapping energy $E_{TR}$.

The trapping energy $E_{TR}$ of the molecule 101 inside the gap 111 can be estimated. FIG. 2A illustrates a chart 200 for trapping energy $E_{TR}$. The gap 111 size can be defined as d, separation between charges 103 as l, a distance between a reference charge from the first reservoir 105 as δ, and a charge radius as r. For illustrative purposes, the charges 103 can be viewed as disposed on a straight line, and that the charges 103g inside the gap 111 are not hydrated (i.e. there are no solvent molecules on their surface). In addition, the interface between solution 109 and the gap 111 can be viewed as flat. The energy difference for a charge transfer between two half-spaces with different dielectric permittivities $\varepsilon_1$, $\varepsilon_2$ can be described by the well known Born equation:

$$\frac{w_{Born}}{kT} = \frac{q_0}{r}\left(\frac{1}{\varepsilon_2} - \frac{1}{\varepsilon_1}\right) \qquad \text{Equation 1}$$

where $$q_0 = \frac{e_0^2}{2kT\varepsilon_0} = 282 \text{ Å}$$

at room temperature, and $e_0$ is the value of the charge. The energy $w(\delta)$ of a single charge moving through a slab with different permittivity is more complex than Equation 1. For the energy $WS(\delta)$ of an infinite series of charges, the relation is:

$$WS(\delta) = \sum_{n=-\infty}^{+\infty} w(n \cdot l + \delta). \qquad \text{Equation 2}$$

Finally, the trapping energy can be defined as:

$$E_{TR} = \max_{\delta} WS(\delta) - \min_{\delta} WS(\delta). \qquad \text{Equation 3}$$

Figure 2B:
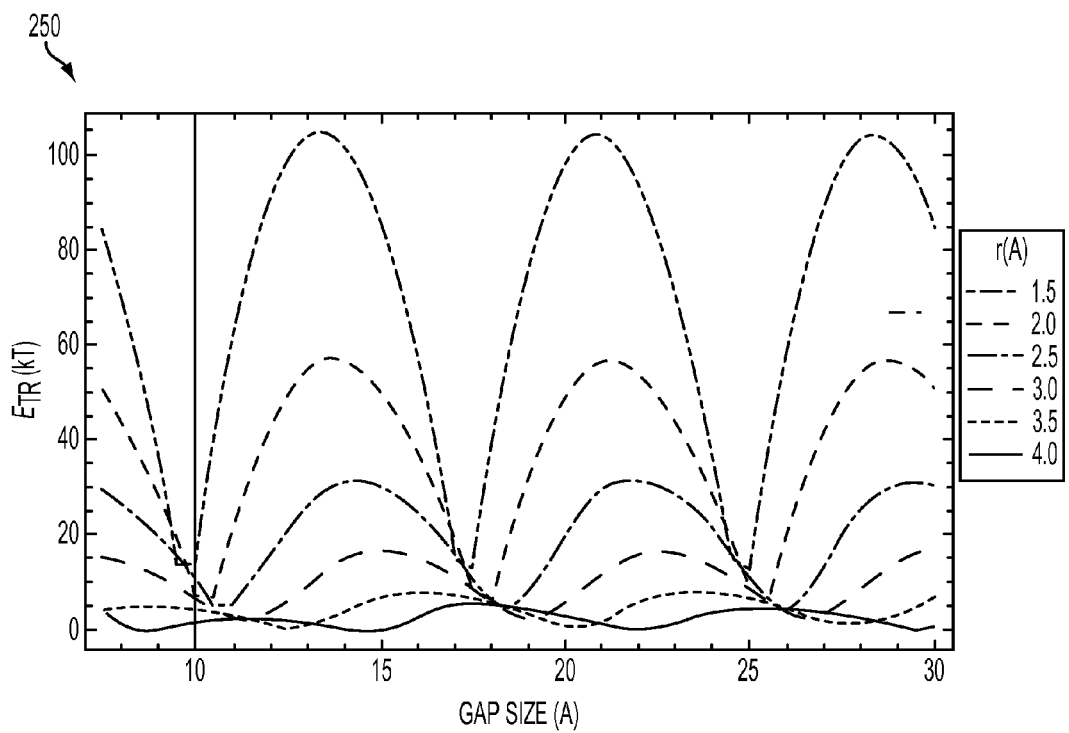
FIG. 2B illustrates a chart that illustrates results of a numerical evaluation.

For numerical estimates, a single stranded DNA molecule solvated in water ($\varepsilon_1=80$) and its segment trapped in the air gap ($\varepsilon_2=1$) can be illustrated. A single electron charge can be located at backbone's phosphate group and these groups are separated by l=7.5 A. FIG. 2B illustrates a chart 250 that illustrates numerical evaluation of Equation 3 as a function of gap size d. The energy is expressed in units of k T, where k is Boltzmann constant, and T is absolute temperature. $E_{TR}(d)$ is a periodic function of gap size d with maxima corresponding to the strongest trapping and minima corresponding to the weakest trapping. In practice, for the best trapping the gap 111 size is controlled so that $E_{TR}$ is located near its maximum. Multiple $E_{TR}$ curves on FIG. 2B correspond to different charge radius r, which serves as a parameter in exemplary embodiments. For typical values r=2-3 A, $E_{TR}$ is tens of k T, which is quite sufficient to trap the molecule 101 against its thermal fluctuations.

Figure 3:
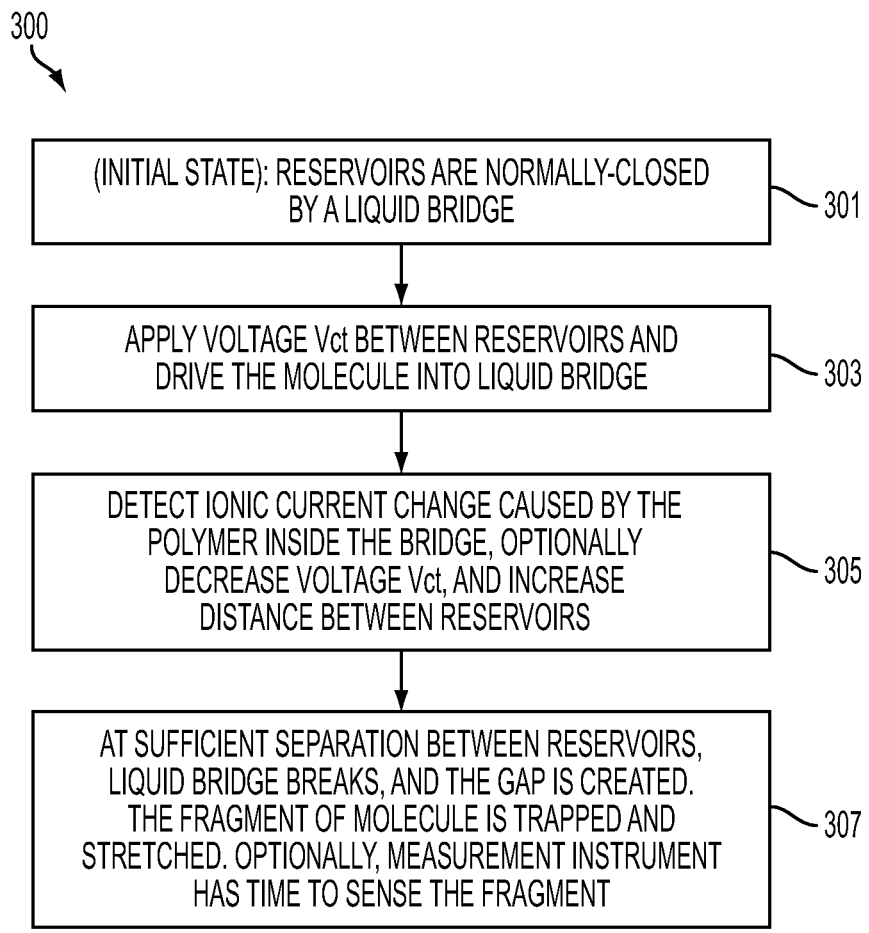
FIG. 3 illustrates a method for trapping a molecule in accordance with exemplary embodiments.
Figure 4:
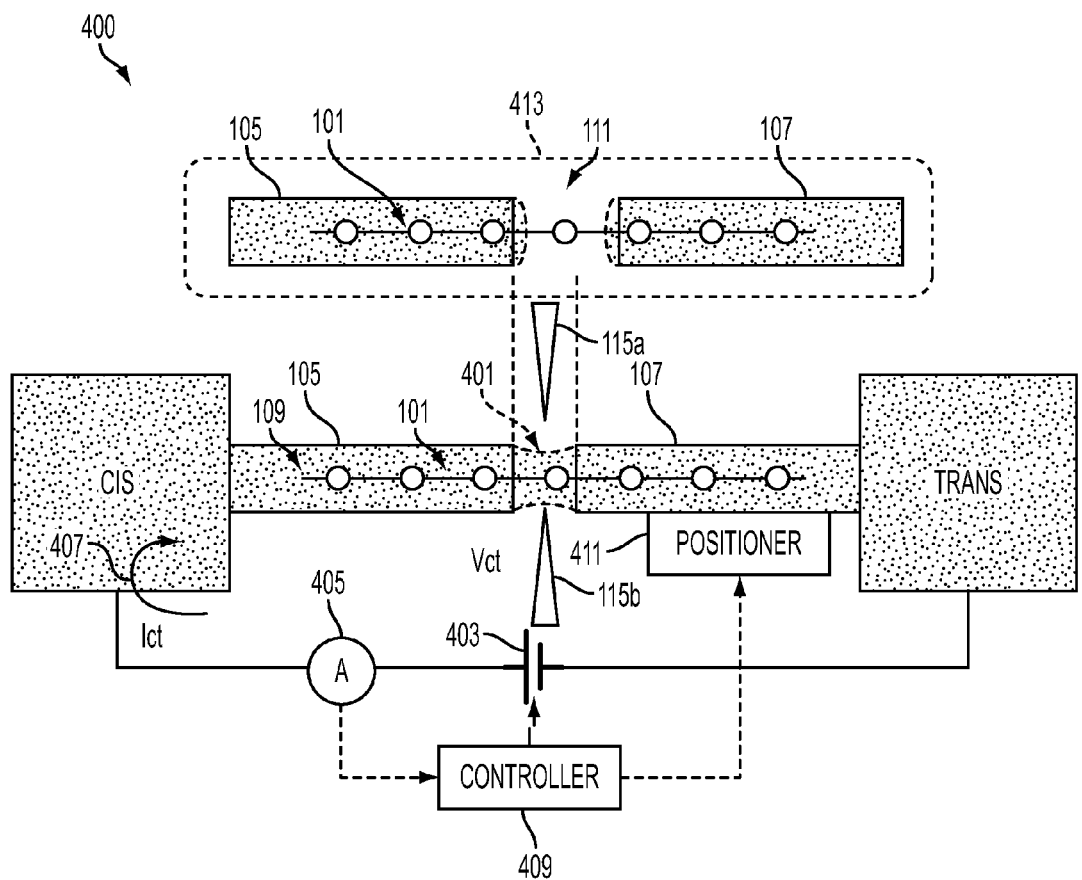
FIG. 4 diagrammatically illustrates an exemplary system for trapping a segment of a molecule.

FIG. 1 illustrates a generalization of the type of system that can be implemented in accordance with exemplary embodiments. There are several modifications to the system 100 in accordance with exemplary embodiments. In addition, each exemplary system can implement a method to trap a molecule in accordance with exemplary embodiments. For example, FIG. 3 illustrates a method 300 for trapping a molecule in accordance with exemplary embodiments. FIG. 4 diagrammatically illustrates an exemplary system 400 for trapping a segment of a molecule. The system 400 can include the first and second reservoirs 105, 107, each of the reservoirs 105, 107 filled with the solution 109. For illustrative purposes, the reservoirs 105, 107 each include a CIS and TRANS side. It is understood that illustrating CIS and TRANS sides of the molecules is illustrative only and not limiting. The system 400 further illustrates a fluid (liquid) bridge 401 that bridges the gap 111 shown in FIG. 1. It can be appreciated that surface tension between the solution 109 in the first reservoir 105 and the second reservoir 107 can create the fluid (liquid) bridge 401. The fluid (liquid) bridge 401 can be controlled by adjusting the width of the gap 111 by a mechanical positioner 411 that can increase and decrease the distance (i.e., the gap 111) between the reservoirs 105, 107. In addition, a voltage source 403 can be disposed and in electrical communication with the reservoirs 105, 107. An ammeter 405 can be disposed in series with the voltage source 403. It can be appreciated that the reservoirs 105, 107, the fluid (liquid) bridge 401, the voltage source 403 and the ammeter 405 form a circuit as further described herein. When the circuit is complete, that is, when the fluid (liquid) bridge 401 is formed, an ionic current 407, Ict, can flow within the circuit. The system 400 can further include a controller 409 (e.g., a computing system) that can control the positioner 411 and the voltage source 403. The controller 409 can further measure the ionic current 407, Ict, from the ammeter 405.

Referring again to FIG. 3, block 301 defines an initial state of the system 400. In the initial state at block 301, the fluid (liquid) bridge 401 connects reservoirs 105, 107. For illustrative purposes, the reservoirs 105, 107 in the initial state at block 301 can be called "normally-closed" from mechanical relay terminology. At block 303, the controller 409 can apply a voltage difference Vct from the voltage source 403 between the reservoirs 105, 107, which drives the molecule 101 through the fluid (liquid) bridge 401. The ionic current 407, Ict, between the reservoirs 105, 107 is measured by ammeter 405, and recorded by the controller 409. The molecule 101 inside the bridge changes the ionic current 407, Ict. Thus at block 305, the controller 409 can further detect and record the change of ionic current 407, Ict. The controller 409 can also decrease the voltage difference Vct to slow down the speed of translocation of the molecule, and direct the positioner 411 to increase the distance between reservoirs 105, 107. At block 307, at sufficient separation between the reservoirs 105, 107, the fluid (liquid) bridge 401 breaks and the gap 111 is created, as shown by dashed box 413 in FIG. 4. In addition, the segment of the molecule 101 inside the gap 111 is stretched and trapped, allowing the measurement instrument 115a, 115b to sense the segment.

Figure 5:
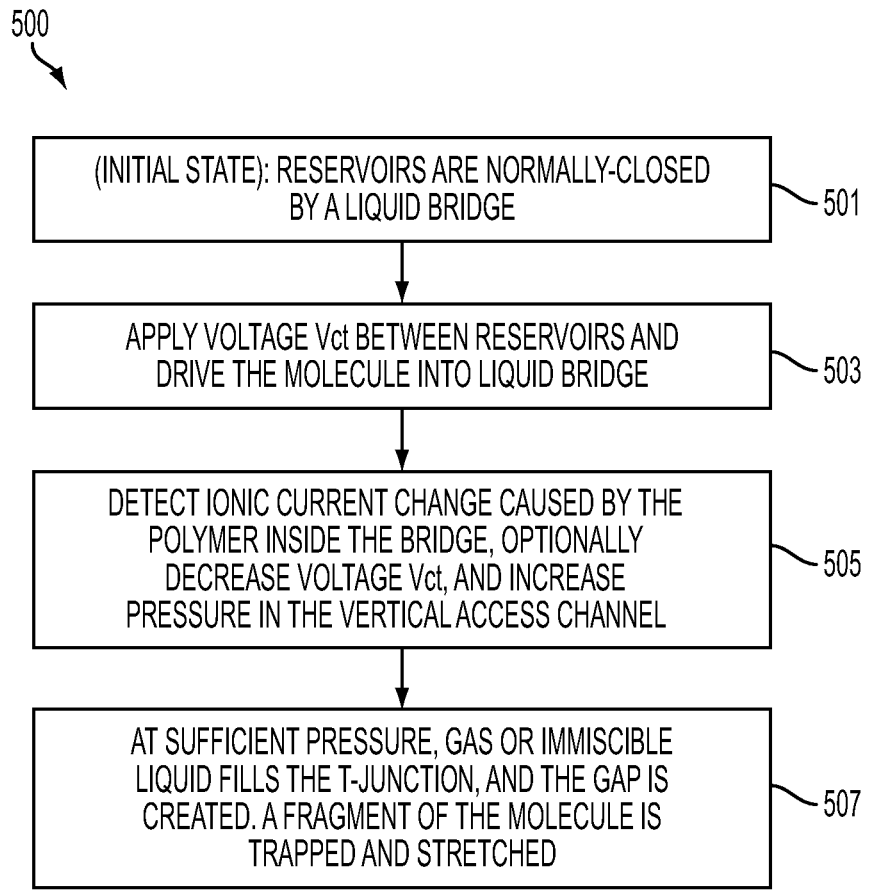
FIG. 5 illustrates another method for trapping a molecule in accordance with exemplary embodiments.
Figure 6:
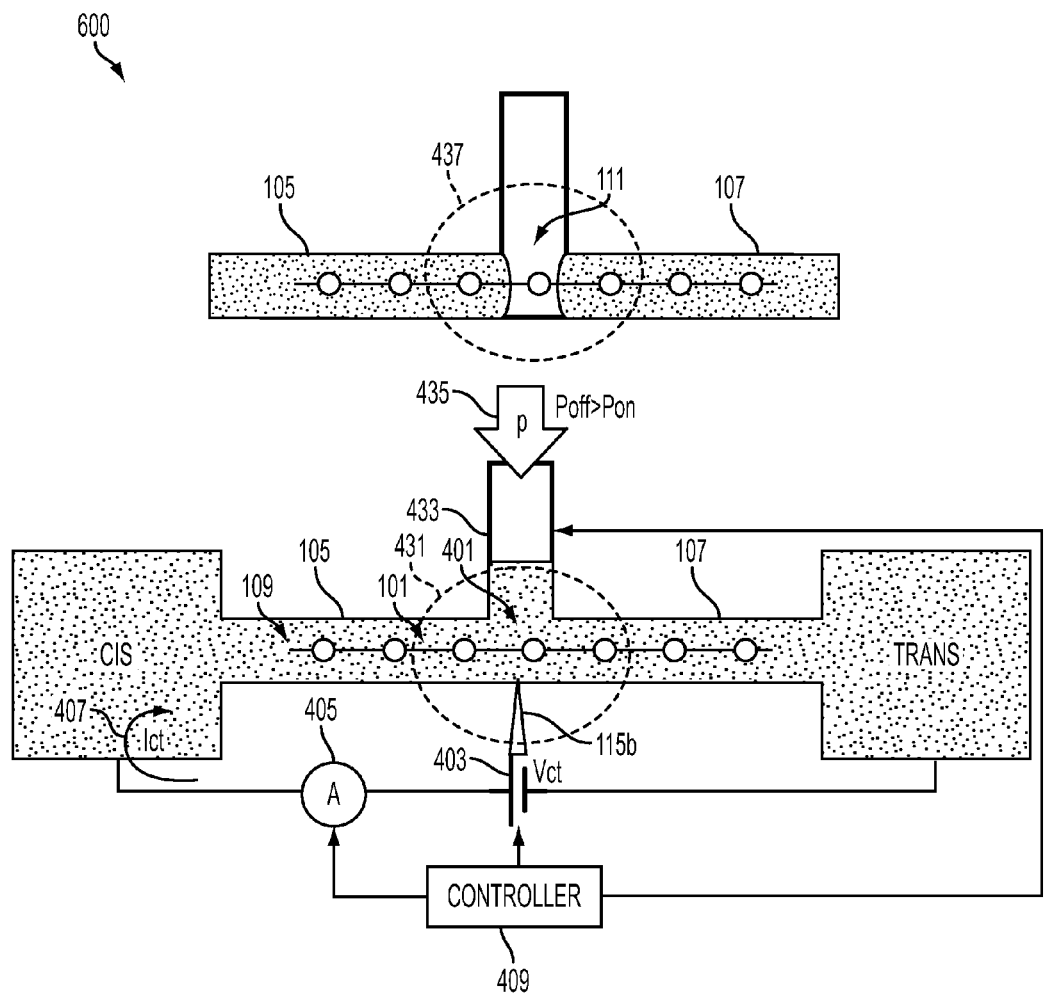
FIG. 6 diagrammatically illustrates another exemplary system for trapping a segment of a molecule.

FIG. 5 illustrates a method 500 for trapping a molecule in accordance with exemplary embodiments. FIG. 6 diagrammatically illustrates an exemplary system 600 for trapping a segment of a molecule. The system 600 can include the first and second reservoirs 105, 107, each of the reservoirs 105, 107 filled with the solution 109. For illustrative purposes, the reservoirs 105, 107 each include a CIS and TRANS side. It is understood that illustrating CIS and TRANS sides of the molecules is illustrative only and not limiting. The system 600 further includes a T-junction 431 that bridges the reservoirs 105, 107. The system 600 further includes a vertical channel 433 that is in fluid (liquid) communication with the reservoirs 105, 107 and the T-junction 431. In addition the vertical channel 433 can be filled with a gas or an immiscible fluid (liquid). A fluid (liquid) bridge 401 is disposed in the T-junction 431. In exemplary embodiments, the fluid (liquid) bridge 401 can be controlled by adjusting the width of the gap 111 by applying pressure, from a pressure (i.e., pneumatic) source 435, within the vertical channel 433. The voltage source 403 can be disposed and in electrical communication with the reservoirs 105, 107. An ammeter 405 can be disposed in series with the voltage source 403. It can be appreciated that the reservoirs 105, 107, the fluid (liquid) bridge 401, the voltage source 403 and the ammeter 405 form a circuit. When the circuit is complete, that is, when the fluid (liquid) bridge 401 is formed, an ionic current 407, Ict, can flow within the circuit. The system 600 can further include a controller 409 (e.g., a computing system) that can control the pressure source 435 and the voltage source 403. The controller 409 can further measure the ionic current 407, Ict, from the ammeter 405.

Referring again to FIG. 5, block 501 defines an initial state of the system 600. In the initial state at block 501, the fluid (liquid) bridge 401 connects reservoirs 105, 107. For illustrative purposes, the reservoirs 105, 107 in the initial state at block 501 can be called "normally-closed" from mechanical relay terminology. At block 503, the controller 409 can apply a voltage difference Vct from the voltage source 403 between the reservoirs 105, 107, which drives the molecule 101 through the fluid (liquid) bridge 401. The ionic current 407, Ict, between the reservoirs 105, 107 is measured by ammeter 405, and recorded by the controller 409. The molecule 101 inside the bridge changes the ionic current 407, Ict. Thus at block 505, the controller 409 can further detect and record the change of ionic current 407, Ict. The controller 409 can also decrease the voltage difference Vct to slow down the speed of molecule translocation, and direct the pressure source 435. At block 507, at sufficient pressure between the reservoirs 105, 107, enough gas or immiscible fluid (liquid) fills the T-junction 431, breaking the fluid (liquid) bridge 401, and creating the gap 111, as shown by dashed box 437 in FIG. 6. In addition, the segment of the molecule 101 inside the gap 111 is stretched and trapped, allowing the measurement instrument 115b to sense the segment.

As described herein, there are several modifications that can be made to the exemplary systems as illustrated in FIGS. 1, 3 and 6. In another example, in exemplary embodiments, electro-wetting can control the generation of a molecule trapping gap. Electro-wetting is the phenomenon of the change in the wetting properties of a fluid (liquid) droplet on a solid surface by the application of an electric field. Electro-wetting can make a non-wetting fluid (liquid) droplet which will be nearly spherical in shape to wet a solid surface spreading as a thin layer over it. Electro-wetting has been applied to transport small volumes of fluids (liquids) in a controlled way in microfluidic chips and also to develop electrical picture displays operated by controlling the spatial distribution of tiny fluid (liquid) droplets.

Figure 7:
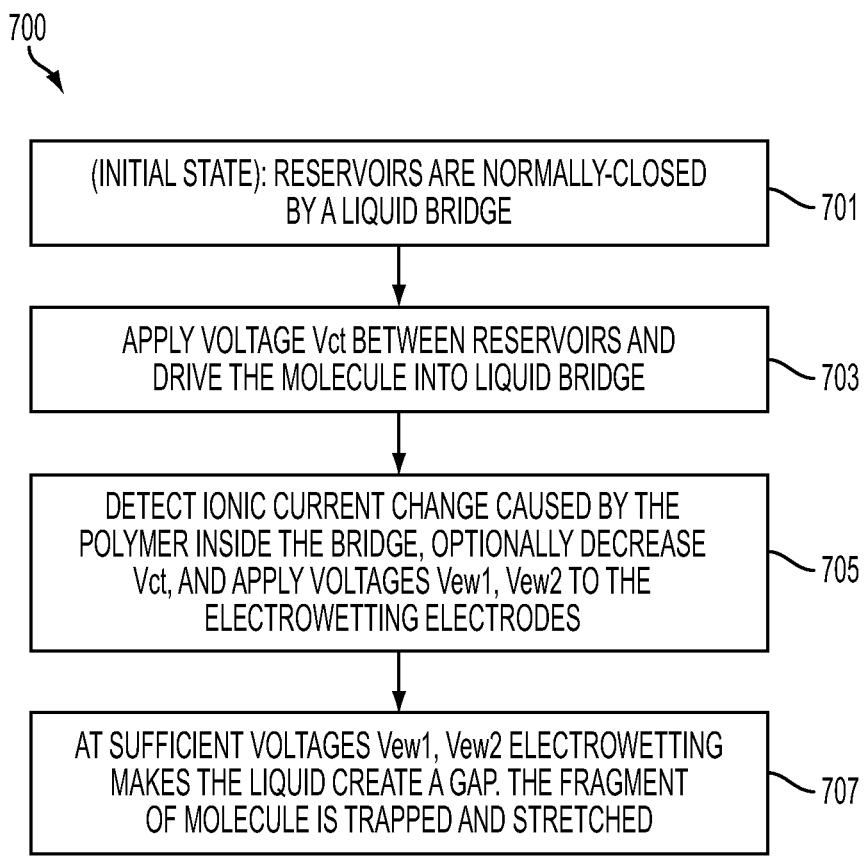
FIG. 7 illustrates another method for trapping a molecule in accordance with exemplary embodiments.
Figure 8:
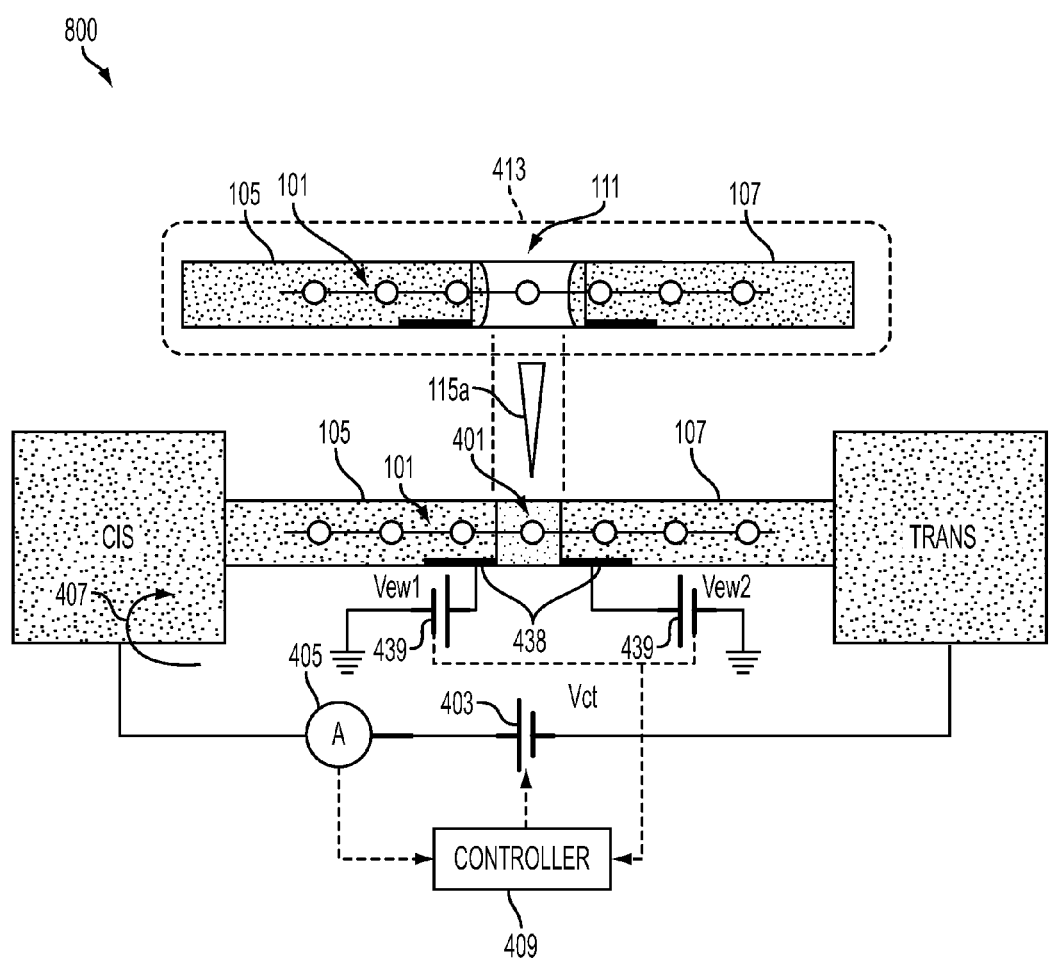
FIG. 8 diagrammatically illustrates another exemplary system for trapping a segment of a molecule.

FIG. 7 illustrates a method 700 for trapping a molecule in accordance with exemplary embodiments. FIG. 8 diagrammatically illustrates an exemplary system 800 for trapping a segment of a molecule. The system 800 can include the first and second reservoirs 105, 107, each of the reservoirs 105, 107 filled with the solution 109. In exemplary embodiments, the reservoirs 105, 107 are part of a single continuous channel or tube. For illustrative purposes, the reservoirs 105, 107 each include a CIS and TRANS side illustrating the cis and trans sides of the molecule 101. It is understood that illustrating CIS and TRANS sides of the molecules is illustrative only and not limiting. The system 400 further illustrates a fluid (liquid) bridge 401 that bridges the gap 111 shown in FIG. 1. The fluid (liquid) bridge 401 is shown with different shading from the reservoirs 105, 107 as further described herein. The fluid (liquid) bridge 401 can be controlled by adjusting the width of the gap 111 by applying electro-wetting principles that can increase and decrease the distance (i.e., the gap 111) between the reservoirs 105, 107. As such, the system 800 can include electro-wetting electrodes 438 that are electrically coupled to electro-wetting voltage sources 439. In this way, electro-wetting voltages $V_{ew1}$, $V_{ew2}$ can be applied to the electro-wetting electrodes 438 to create a vapor pocket, and thus the gap 401 between the reservoirs 105, 107. In exemplary embodiments, the electro-wetting electrodes 438 can be made with a metal layer and coated with an insulator to prevent any leakage current entering the solution 109 through these electrodes. The system 800 can further include a voltage source 403 disposed and in electrical communication with the reservoirs 105, 107. The insulator for the electro-wetting electrodes 438 can also isolate the electro-wetting electrodes 438 electrically from the voltage source 403 that drives the molecule 101. An ammeter 405 can be disposed adjacent to the voltage source 403. It can be appreciated that the reservoirs 105, 107, the fluid (liquid) bridge 401, the voltage source 403 and the ammeter 405 form a circuit as further described herein. When the circuit is complete, that is, when the fluid (liquid) bridge 401 is formed, an ionic current 407, Ict, can flow within the circuit. The system 800 can further include a controller 409 (e.g., a computing system) that can control the voltage source 403 and the electro-wetting voltage sources 439. The controller 409 can further measure the ionic current 407, Ict, from the ammeter 405.

Referring again to FIG. 7, block 701 defines an initial state of the system 800. In the initial state at block 701, the fluid (liquid) bridge 401 connects reservoirs 105, 107. Since the reservoirs 105, 107 are part of a single continuous channel, the fluid (liquid) bridge 401 is shown in different shading than the reservoirs for illustrative purposes. In addition, the reservoirs 105, 107 in the initial state at block 701 can be called "normally-closed" from mechanical relay terminology. At block 703, the controller 409 can apply a voltage difference Vct from the voltage source 403 between the reservoirs 105, 107, which drives the molecule 101 through the fluid (liquid) bridge 401. The ionic current 407, Ict, between the reservoirs 105, 107 is measured by ammeter 405, and recorded by the controller 409. The molecule 101 inside the bridge changes the ionic current 407, Ict. Thus at block 705, the controller 409 can further detect and record the change of ionic current 407, Ict. The controller 409 can also decrease the voltage difference Vct to slow down the speed of molecule translocation, and increases the voltages $V_{ew1}$, $V_{ew2}$ to increase the distance between reservoirs 105, 107. At block 707, at sufficient separation between the reservoirs 105, 107, the fluid (liquid) bridge 401 breaks, and the gap 111 is created, as shown by dashed box 413 in FIG. 4. In addition, the segment of the molecule 101 inside the gap 111 is stretched and trapped, allowing the measurement instrument 115a to sense the segment.

Figure 9:
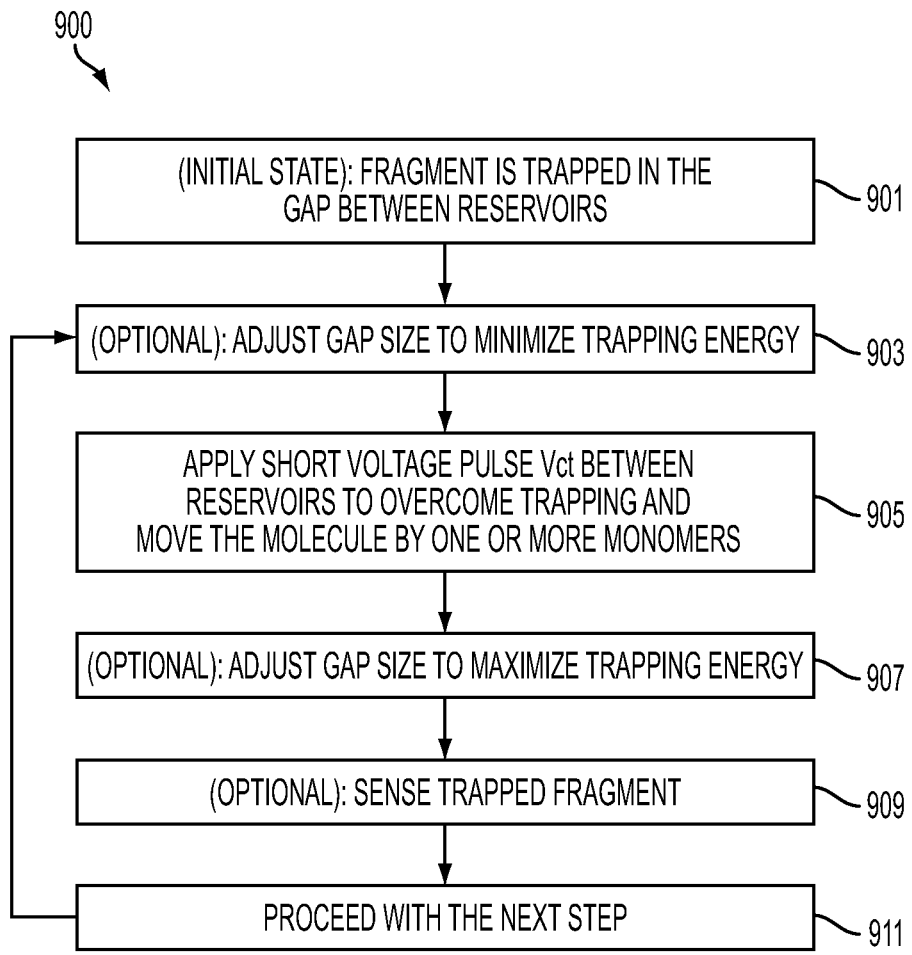
FIG. 9 illustrates a flow chart for a translocation method of a trapped molecule in accordance with exemplary embodiments.

FIG. 9 illustrates a flow chart for a translocation method 900 of a trapped molecule 101 in accordance with exemplary embodiments. The systems and methods described herein described trapping the molecule 101 within a gap 111. Once the molecule is trapped, each individual charged particle (i.e., nucleotide) of the molecule 101 can be appropriately measured and then translocated. As such, at an initial state at block 901, a segment of the molecule 101 is trapped within the gap 111 as applied with one of the methods and systems as described with respect to FIGS. 3-8. At block 903, to facilitate translocation, the gap size can be adjusted to minimize $E_{TR}$. As described herein, the adjustment of the size of the gap 111 can be performed advantageously by one of the electrical (e.g., electro-wetting), pressure mechanical methods and systems described herein. At block 905, the controller 409 directs the voltage source 403 to apply a voltage pulse large enough to overcome the trapping energy of the gap 111 and move the molecule 101 (e.g., by one or more monomers). As such, the molecule 101 starts to translocate through the gap 111. The duration of the voltage pulse from the voltage source 403 controls the extent of its translocation. It can be appreciated that the magnitude and duration of the voltage pulse can be selected so that it is short enough to move the molecule 101 by just one particle (e.g., monomer). At block 907, the gap 11 can be adjusted once again to increase the trapping energy of the gap 111, as described herein. By adjusting the gap 111, the molecule 101 can be locked into the new position. At block 909, the trapped segment of the molecule 101 can be sensed and/or measured by the measurement instrument 115a, 115b. Multiple translocations in forward and/or reverse directions can be repeated at block 911.

Figure 10:
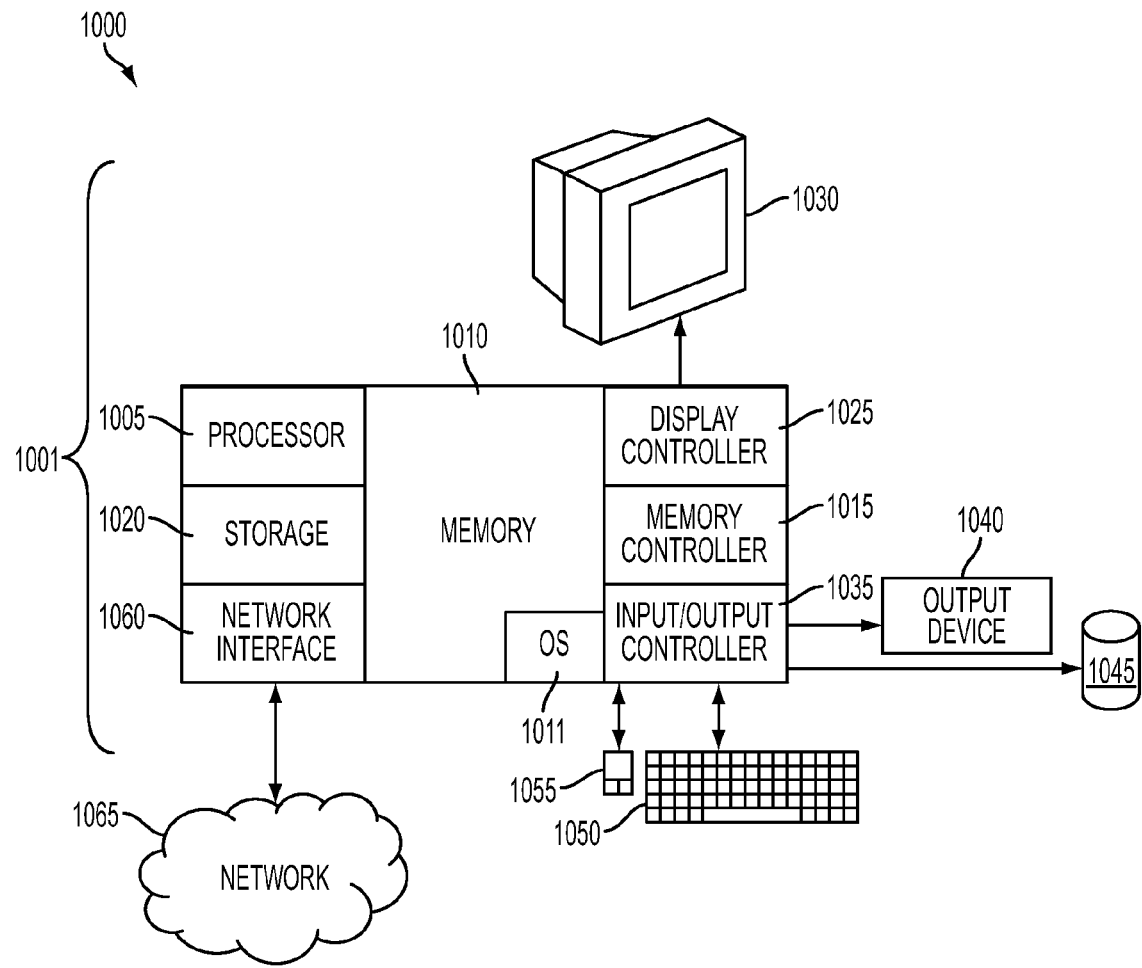
FIG. 10 illustrates an exemplary embodiment of a computing system that can be implemented for the molecule trapping and translocation methods.

The controller 409 can be any suitable computing system that can have various peripherals as now described. FIG. 10 illustrates an exemplary embodiment of a computing system 1000 that can be implemented for the molecule trapping and translocation methods described herein. The methods described herein can be implemented in software (e.g., firmware), hardware, or a combination thereof. In exemplary embodiments, the methods described herein are implemented in software, as an executable program, and is executed by a special or general-purpose digital computer, such as a personal computer, workstation, minicomputer, or mainframe computer. The system 1000 therefore includes general-purpose computer 1001.

In exemplary embodiments, in terms of hardware architecture, as shown in FIG. 10, the computer 1001 includes a processor 1005, memory 1010 coupled to a memory controller 1015, and one or more input and/or output (I/O) devices 1040, 1045 (or peripherals) that are communicatively coupled via a local input/output controller 1035. The input/output controller 1035 can be, but is not limited to, one or more buses or other wired or wireless connections, as is known in the art. The input/output controller 1035 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1005 is a hardware device for executing software, particularly that stored in memory 1010. The processor 1005 can be any custom made or commercially available processor, a central processing unit (CPU), an auxiliary processor among several processors associated with the computer 1001, a semiconductor based microprocessor (in the form of a microchip or chip set), a macroprocessor, or generally any device for executing software instructions.

The memory 1010 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc. Moreover, the memory 1010 may incorporate electronic, magnetic, optical, and/or other types of storage media. Note that the memory 1010 can have a distributed architecture, where various components are situated remote from one another, but can be accessed by the processor 1005.

The software in memory 1010 may include one or more separate programs, each of which comprises an ordered listing of executable instructions for implementing logical functions. In the example of FIG. 10, the software in the memory 1010 includes the molecule trapping and translocation methods described herein in accordance with exemplary embodiments and a suitable operating system (OS) 1011. The OS 1011 essentially controls the execution of other computer programs, such the molecule trapping and translocation systems and methods as described herein, and provides scheduling, input-output control, file and data management, memory management, and communication control and related services.

The molecule trapping and translocation methods described herein may be in the form of a source program, executable program (object code), script, or any other entity comprising a set of instructions to be performed. When a source program, then the program needs to be translated via a compiler, assembler, interpreter, or the like, which may or may not be included within the memory 1010, so as to operate properly in connection with the OS 1011. Furthermore, the molecule trapping and translocation methods can be written as an object oriented programming language, which has classes of data and methods, or a procedure programming language, which has routines, subroutines, and/or functions.

In exemplary embodiments, a conventional keyboard 1050 and mouse 1055 can be coupled to the input/output controller 1035. Other output devices such as the I/O devices 1040, 1045 may include input devices, for example but not limited to a printer, a scanner, microphone, and the like. Finally, the I/O devices 1040, 1045 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 1000 can further include a display controller 1025 coupled to a display 1030. In exemplary embodiments, the system 1000 can further include a network interface 1060 for coupling to a network 1065. The network 1065 can be an IP-based network for communication between the computer 1001 and any external server, client and the like via a broadband connection. The network 1065 transmits and receives data between the computer 1001 and external systems. In exemplary embodiments, network 1065 can be a managed IP network administered by a service provider. The network 1065 may be implemented in a wireless fashion, e.g., using wireless protocols and technologies, such as WiFi, WiMax, etc. The network 1065 can also be a packet-switched network such as a local area network, wide area network, metropolitan area network, Internet network, or other similar type of network environment. The network 1065 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 1001 is a PC, workstation, intelligent device or the like, the software in the memory 1010 may further include a basic input output system (BIOS) (omitted for simplicity). The BIOS is a set of essential software routines that initialize and test hardware at startup, start the OS 1011, and support the transfer of data among the hardware devices. The BIOS is stored in ROM so that the BIOS can be executed when the computer 1001 is activated.

When the computer 1001 is in operation, the processor 1005 is configured to execute software stored within the memory 1010, to communicate data to and from the memory 1010, and to generally control operations of the computer 1001 pursuant to the software. The molecule trapping and translocation methods described herein and the OS 1011, in whole or in part, but typically the latter, are read by the processor 1005, perhaps buffered within the processor 1005, and then executed.

When the systems and methods described herein are implemented in software, as is shown in FIG. 10, the methods can be stored on any computer readable medium, such as storage 1020, for use by or in connection with any computer related system or method.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of a code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In exemplary embodiments, where the molecule trapping and translocation methods are implemented in hardware, the molecule trapping and translocation methods described herein can implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A molecule trapping method, comprising:
   forming a fluid bridge between a first reservoir and a second reservoir;
   translocating a molecule from the first reservoir to the second reservoir through the fluid bridge;
   detecting when a segment of the molecule is in the fluid bridge;
   breaking the fluid bridge and forming a gap between the first and the second reservoirs, thereby trapping a segment of the molecule in the gap; and
   making measurements on the segment of the molecule,
   wherein the gap is formed by at least one of a vacuum, a gas and an immiscible fluid.

2. The method as claimed in claim 1 wherein translocating the molecule in the fluid bridge comprises applying a first voltage across the first reservoir and the second reservoir.

3. The method as claimed in claim 2 further comprising increasing the first voltage to drive the segment of the molecule.

4. The method as claimed in claim 2 further comprising decreasing the first voltage to slow the segment of the molecule.

5. The method as claimed in claim 1 further comprising measuring an ionic current in the first reservoir and the second reservoir to detect entry of the molecule in the fluid bridge.

6. The method as claimed in claim 1 wherein trapping the molecule at a first location within the first reservoir and second reservoir comprises generating a gap between the first reservoir and the second reservoir.

7. The method as claimed in claim 6 wherein the gap is generated by pneumatically breaking the fluid bridge.

* * * * *